US006669664B2

(12) United States Patent
Slate et al.

(10) Patent No.: US 6,669,664 B2
(45) Date of Patent: Dec. 30, 2003

(54) VACUUM CONTROL CYCLE FOR JET INJECTOR

(75) Inventors: John B. Slate, San Diego, CA (US); Michael W. Burk, San Marcos, CA (US); Lanny A. Gorton, San Diego, CA (US)

(73) Assignee: Avant Drug Delivery Systems, Inc., San Diego, CA (US)

( * ) Notice: Subject to any disclaimer, the term of this patent is extended or adjusted under 35 U.S.C. 154(b) by 301 days.

(21) Appl. No.: 09/949,484

(22) Filed: Sep. 7, 2001

(65) Prior Publication Data

US 2003/0050592 A1 Mar. 13, 2003

(51) Int. Cl.[7] .................................................. A61M 5/30
(52) U.S. Cl. ........................................................ 604/68
(58) Field of Search ...................................... 604/68–72

(56) References Cited

U.S. PATENT DOCUMENTS

| | | |
|---|---|---|
| 3,640,277 A | 2/1972 | Adelberg |
| 4,059,107 A | 11/1977 | Iriguchi et al. |
| 4,421,508 A | 12/1983 | Cohen |
| 4,623,332 A | 11/1986 | Lindmayer et al. |
| 4,680,027 A | 7/1987 | Parsons et al. |
| 4,722,728 A | 2/1988 | Dixon |
| 4,874,367 A | 10/1989 | Edwards |
| 5,024,656 A | 6/1991 | Gasaway et al. |
| 5,190,523 A | 3/1993 | Lindmayer |
| 5,312,335 A | 5/1994 | McKinnon et al. |
| 5,399,163 A | 3/1995 | Peterson et al. |
| 5,480,381 A | 1/1996 | Weston |
| 5,911,703 A | 6/1999 | Slate et al. |

FOREIGN PATENT DOCUMENTS

| | | |
|---|---|---|
| EP | 0 347 190 | 6/1989 |
| WO | WO 86/01728 | 3/1986 |

*Primary Examiner*—Michael J. Hayes
(74) *Attorney, Agent, or Firm*—Nydegger & Associates

(57) ABSTRACT

A vacuum control system for a jet injector includes a power source and vacuum pump for creating suction at the injector tip. The injector includes a drive bar to expel medicament into the patient. Before injection the drive bar and an inner barrel are separated from each other, and at the end of the injection the drive bar contacts the inner barrel. A user operable switch that is moveable between an ON position and an OFF position is also provided. The power source, vacuum pump, drive bar, inner barrel and user operable switch are all electrically connected via an electrical circuit. The electrical circuit is configured to activate the vacuum pump when the user operable switch is in the ON position and the drive bar is separated from the inner barrel, and to deactivate the vacuum pump when the drive bar contacts the inner barrel.

21 Claims, 4 Drawing Sheets

VACUUM CONTROL CYCLE FOR JET INJECTOR

FIELD OF THE INVENTION

The present invention pertains generally to injectors for delivering a medicament into a patient. More particularly, the present invention pertains to needleless injectors having a vacuum system for applying a suction at the interface between the injector and the skin of the patient. The present invention is particularly, but not exclusively, useful for controlling the vacuum system of a needleless injector during the administration of a dose of medicament to a patient.

BACKGROUND OF THE INVENTION

Historically, most injections have been performed using traditional hypodermic syringes. More recently, diseases caused by the transmission of bloodborne pathogens such as HIV and hepatitis have caused the health care industry to closely examine the safety of traditional hypodermic syringes. Because of the fatal nature of AIDS and the lack of a suitable cure, exposing health care workers to contaminated needles and other sharps is now considered unacceptable. Needleless injectors offer an alternative to traditional hypodermic syringes.

Needleless injectors are less likely to accidentally transmit bloodborne pathogens from a patient to a health care worker than traditional hypodermic syringes for several reasons. First, only the medicament and not the needleless injector actually penetrates the patient, thus, the needleless injector is unlikely to become contaminated with bloodborne pathogens during use. Also, a contaminated needleless injector is unlikely to transmit a bloodborne pathogen to a health care worker because the needleless injector does not have any sharp surfaces to expose the blood of the health care worker. Additionally, accidental needlesticks often occur while capping or covering the needle. Thus, these types of accidents are obviated by the use of a needleless injector.

In overview, a needleless injector typically includes a chamber for holding an injectable medicament. At the tip of the injector, an opening is provided in the chamber for transferring medicament from the chamber and into the patient. A plunger and a mechanism for rapidly forcing the plunger into the chamber are generally included to force the medicament through the opening and out the tip of the injector. In use, the tip of the injector is placed in contact with the skin of the patient and the plunger is forced into the chamber. In response, the medicament flows through the opening and out of the tip of the injector, first creating a hole in the skin of the patient. Once a hole in the skin is created, the remaining medicament flows though the hole and into the patient.

Important for the present invention, suction can be used to hold the tip of the injector against the skin. For example, U.S. Pat. No. 5,911,703 entitled "Two-Stage Fluid Medicament Jet Injector" that issued to Slate et al. on Jun. 15, 1999 and which is assigned to the same assignee as the present invention, discloses an injector with an integral suction compartment for pulling the skin against the injector tip. As disclosed, the suction compartment functions to create a seal between the skin area and the injector tip without having to compress the skin area and underlying tissue. Further, the use of a suction compartment can prevent lacerations that can be caused when the injector tip moves relative to the skin during an injection. Also, the suction compartment can function to create a subcutaneous pocket facilitating infusion of the medicament. Another important function of the suction compartment is to provide a seal around the tip of the syringe to enable slow delivery of the medicament.

It is apparent from the above discussion that inadvertent triggering of the injector before the injector is positioned and the suction is applied should be avoided. Also, during an injection, the suction should be maintained to ensure a stable interface between the injector tip and the skin. Thus, control of the vacuum system to provide suction at the skin/injector tip interface is crucial to ensuring a safe, efficient medicament transfer using a needleless injector.

In light of the above, it is an object of the present invention to provide a vacuum control system for a needleless injector in which a single control movement by the user releases a mechanical trigger lock and activates the vacuum motor. Another object of the present invention is to provide a vacuum control system for a needleless injector that is configured to deactivate the vacuum motor if the vacuum switch is released by the user before the triggering of an injection. It is another object of the present invention to provide a vacuum control system for a needleless injector which maintains suction at the interface between the injector and the skin of the patient during injection of the medicament in spite of the inadvertent release of the vacuum activation switch by the user. It is yet another object of the present invention to provide a vacuum control system for a needleless injector that automatically deactivates the vacuum motor after the injection of the medicament into the patient is completed thereby giving the user an indication that the injection is complete and that it is safe to remove the injector from the skin. Still another object of the present invention is to provide a vacuum control system for a needleless injector that functions over the wide range of voltages produced by a typical battery. Another object of the present invention is to provide a vacuum control system for a needleless injector that provides a steady voltage to the vacuum motor during the injection. Still another object of the present invention is to provide a vacuum control system for a needleless injector that draws a minimal amount of power from the battery during periods between use, when the injector is uncocked. Yet another object of the present invention is to provide a vacuum control system for a needleless injector which is easy to use, relatively simple to implement, and comparatively cost effective.

SUMMARY OF THE PREFERRED EMBODIMENTS

The present invention is directed to a vacuum control system for a jet injector. For the present invention, the control system includes a user operable switch and a mechanical switch. An electrical circuit connects these two switches, with a vacuum pump and a battery to control the vacuum at the injector tip during an injection procedure. In the preferred embodiment of the present invention, the user operable switch also functions as a safety release button for the injector to ensure that a vacuum has been established at the injector tip prior to initiating an injection.

For the present invention, the vacuum control system interacts with a jet injector which has an internal mechanical switch. The mechanical switch is configured to automatically close and thereby shut off the vacuum upon completion of an injection. Specifically, the mechanic switch includes a conductive drive bar that travels within the hollow tube of the injector during an injection. A conductive, inner barrel is positioned near the distal end of the injector tube for contact with the drive bar upon completion of an injection. The contact between the drive bar and inner barrel closes the mechanical switch. A cocking mechanism is provided for repositioning the drive bar back to the proximal end of the tube to allow for a subsequent injection. This movement of the drive bar to the proximal end of the tube opens the mechanical switch.

As described above, the electrical circuit has a first switch and a second switch for controlling the operation of the vacuum system. The first switch is user operable and is moveable between an ON position wherein current flows through the switch (i.e. the first switch is closed) and an OFF position. A return spring is provided to bias the first switch in the OFF position. The second switch is established by the contact of the inner barrel with the drive bar. When the inner barrel contacts the drive bar, the second switch is in the ON position and current flows through the switch (i.e. the second switch is closed). Conversely, when the inner barrel is separated from the drive bar, the second switch is in the OFF position and no current flows through the switch (i.e. the second switch is closed).

For the present invention, the electrical circuit is configured to pass current from the power source to the vacuum pump when the first switch is in its ON position and the second switch is in its OFF position. Further, the electrical circuit is configured to prevent current from passing through the vacuum pump when the first switch is in its ON position and the second switch is in its ON position. Additionally, the electrical circuit is configured to prevent current from passing through the vacuum pump whenever the first switch is in its OFF position.

The user operable switch also functions as a safety release button for a firing cap located at the proximal end of the injector tube. For the present invention, an interlock ring that is rotatable about the longitudinal axis of the tube is interposed between the proximal end of the tube and the firing cap. The interlock ring is attached to the user operable switch for rotation about the longitudinal axis of the tube in response to movements of the user operable switch. A tab projects proximally from the interlock ring for engagement with a slot formed in the firing cap near the distal end of the firing cap. When the user operable switch is depressed (i.e. moved to its ON position), the interlock ring is rotated to align the tab of the interlock ring with the slot of the firing cap. With the slot and tab aligned, the firing cap is armed (i.e. capable of being depressed to release the drive bar). The return spring, which biases the user operable switch in the OFF position, also biases the interlock ring into a position where the tab and slot are misaligned to thereby lock the firing cap whenever the user operable switch is not depressed by the user.

In the operation of the present invention, the jet injector is initially uncocked. In the uncocked configuration, both switches are in the ON position (the reason for this will become apparent below), and consequently, the vacuum pump is inactive. Upon cocking the injector, the cocking mechanism will position and hold the drive bar near the proximal end of tube placing the second switch in the OFF position. Further, the cocking mechanism will move the firing cap until the firing cap is positioned proximally to the interlock ring. As such, the return spring will cause both the user operable switch to move into the OFF position and the interlock ring to move to a position where the tab of the interlock ring and the slot of the firing cap are misaligned. Thus, immediately after cocking the injector, the vacuum pump is inactive (because both switches are OFF) and the firing cap is locked.

Once the injector is in the cocked configuration, the user can position the injector tip to a preselected area of skin and depress and hold the user operable switch. Upon depressing the user operable switch, the vacuum pump will be activated (first switch ON, second switch OFF) to provide suction at the injector tip. Further, as indicated above, the firing cap will be armed. At this point, release of the user operable switch will deactivate the vacuum pump, allowing the user to reposition the injector tip. Specifically, upon release of the user operable switch the return spring will cause both the user operable switch to return to the OFF position and the interlock ring to return to a position where the firing cap will be disarmed and locked.

While the user operable switch is depressed and held by the user, the vacuum pump remains activated and the firing cap remains armed. Thus, by holding the user operable switch ON and depressing the firing cap, the user can inject the medicament. Upon depressing the firing cap, the drive bar is released. Further, depressing the firing cap causes the tab of the interlock ring to extend into the slot in the firing cap. Importantly, this prevents the interlock ring from rotating. As such, after the firing cap is depressed, the user operable switch is held in the ON position due to the inability of the interlock ring to rotate. The consequence of this is that once the user depresses the firing cap, the vacuum pump remains activated for the entire duration of the injection, regardless of the whether the user releases the user operable switch.

As indicated above, depressing the firing cap causes the drive bar to translate along the tube. Specifically, the drive bar travels until it contacts the inner barrel, terminating the injection. This contact with the inner barrel closes the second switch, automatically deactivating the vacuum pump (both switches ON). At this point, the injector is in the uncocked configuration, and after replacing the injected medicament, the above described operation steps can be repeated to perform another injection.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
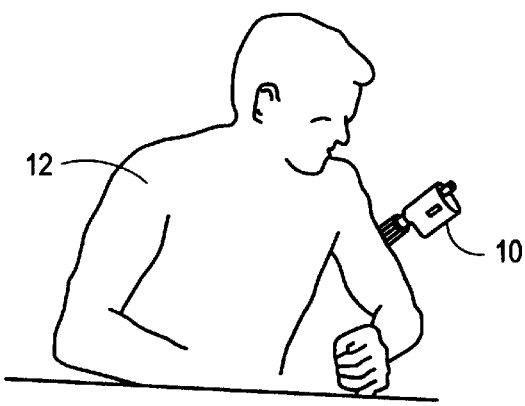
FIG. 1 is a perspective view of a patient using the device of the present invention.
Figure 2:
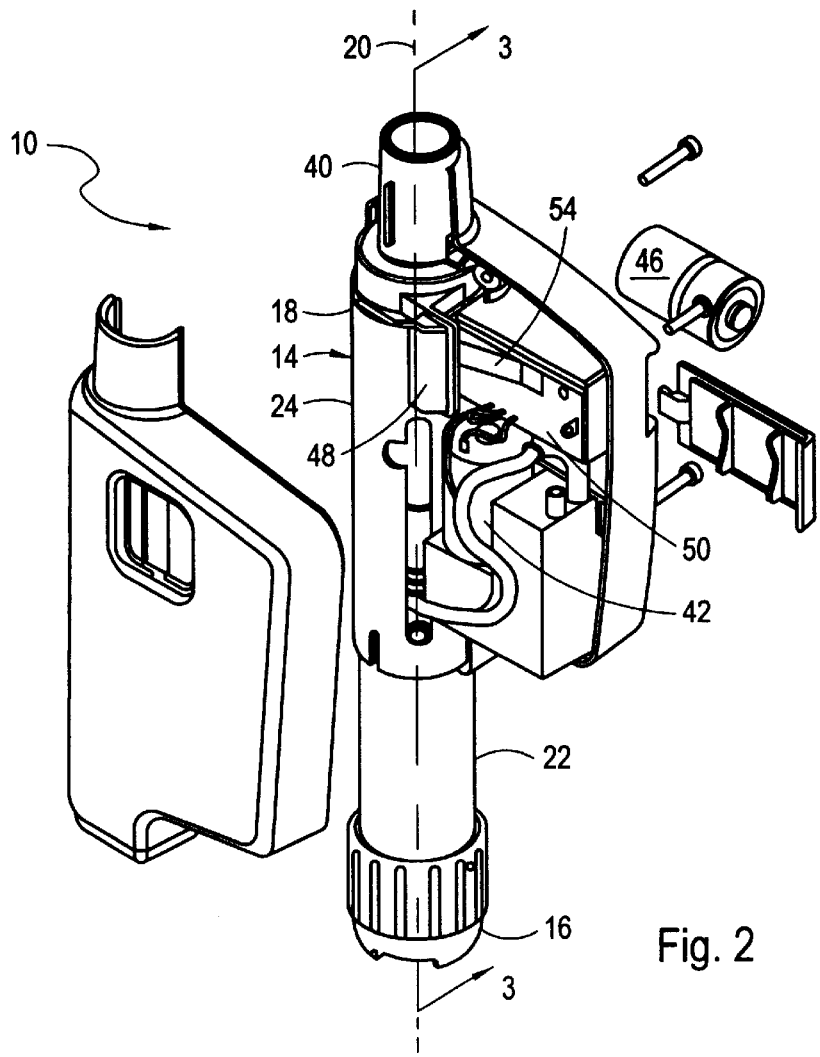
FIG. 2 is a perspective, partially exploded view of the device of the present invention.

Referring to FIG. 1, an injector 10 in accordance with the present invention is shown positioned for an injection on the arm of a patient 12. As shown in FIG. 2, the injector 10 is formed with a tubular housing 14 having a distal end 16, and a proximal end 18. As shown, the tubular housing 14 can include a hollow distal tube 22 and a hollow proximal tube 24, both centered on the axis 20, with the distal tube 22 being sized for insertion into the proximal tube 24.

Figure 3:
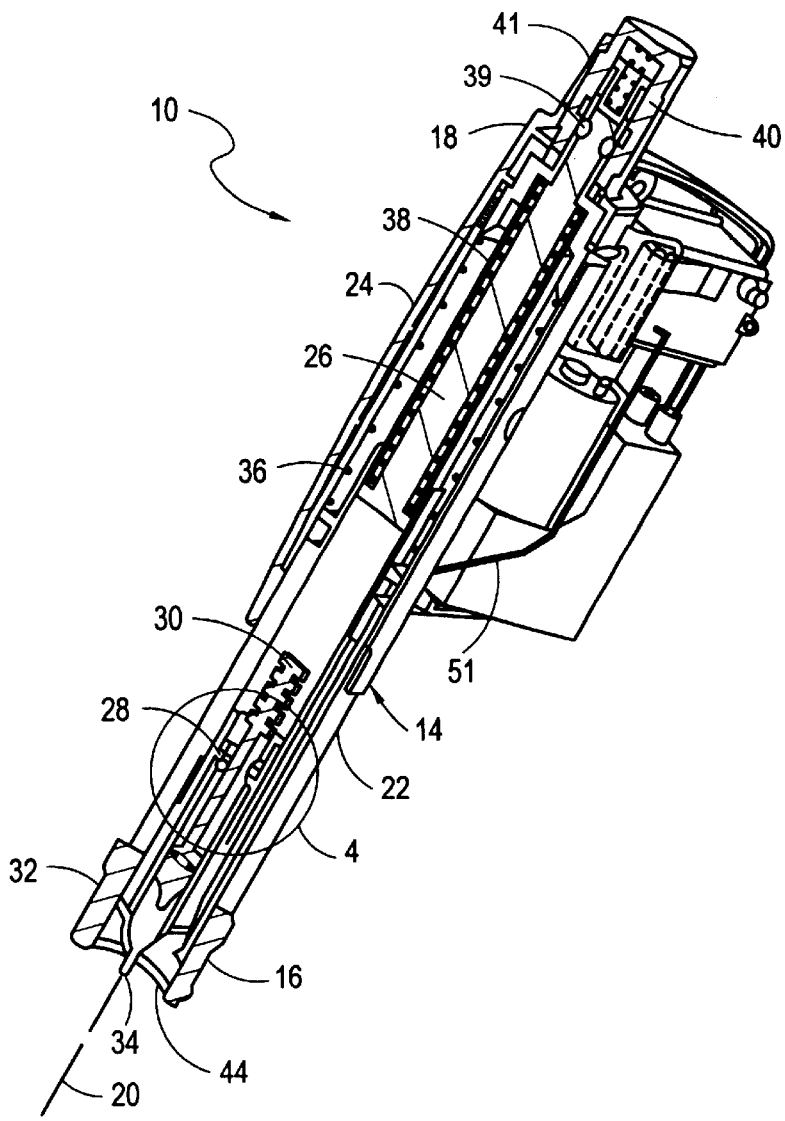
FIG. 3 is a cross-section view of the device of the present invention as seen along line 3—3 in FIG. 2, with the device shown in the cocked configuration.

With cross reference now to FIGS. 2 and 3, it can be seen that a drive bar 26 is disposed within the housing 14 for movement along the longitudinal axis 20 during an injection. Further, as shown, an inner barrel 28 is positioned near the distal end 16 of the housing 14 to limit movement of the drive bar 26 in the distal direction at the completion of an injection. Also shown, a plunger 30 and a medicament chamber 32 are formed in the housing 14 at the proximal end 18. It is to be appreciated that the plunger 30 is insertable into the chamber 32 to expel fluid medicament from the chamber 32 and out through an injector tip 34.

Figure 4:
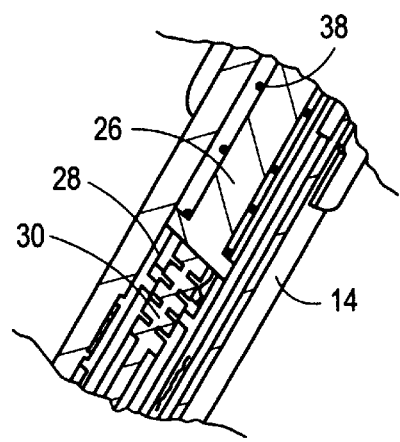
FIG. 4 is a perspective cross-section view of the device of the present invention as seen along line 4—4 in FIG. 3, showing the drive bar in contact with the inner barrel after an injection.

With cross reference to FIGS. 3 and 4, it can be seen that the drive bar 26 translates within the housing 14 from a cocked position (shown in FIG. 3) to a post-injection position (shown in FIG. 4). For the present invention, the distal tube 22 is insertable into the proximal tube 24 to move the drive bar 26 into the cocked position (i.e. near the proximal end 18 of housing 14) immediately before an injection. A cocking return spring 36 is provided to reposition the distal tube 22 relative to the proximal tube 24 after cocking (i.e. to an uncollapsed position). Also shown, a mechanism such as a drive spring 38 is mounted inside the housing 14 for urging the drive bar 26 toward the distal end 16 of the housing 14.

With cross reference to FIGS. 2–4, it can be seen that the injector 10 includes a firing cap 40. As shown, the firing cap 40 is mounted on the housing 14 at the proximal end 18. Bearings 39, firing cap 40 and trigger spring 41 cooperate to engage the drive bar 26 during cocking and hold the drive bar 26 in the cocked position. It is to be appreciated that when the firing cap 40 is depressed by the user, the firing cap 40 disengages the bearings 39 and thereby releases the drive bar 26. Once the drive bar 26 is released, the force applied by the drive spring 38 is sufficient to translate the drive bar 26 along the longitudinal axis 20 of the housing 14 in the distal direction. By comparing FIGS. 3 and 4, it can be seen that the drive bar 26 is free to translate unhindered until the drive bar 26 impacts the plunger 30. The impact between the drive bar 26 and plunger 30 will force the plunger 30 into the medicament chamber 32, expelling medicament from the chamber 32 and through the injector tip 34. After impact, the drive bar 26 continues to translate in the distal direction, forcing the plunger 30 further into the chamber 32 to expel additional medicament, until the drive bar 26 finally contacts the inner barrel 28. Upon contact with the inner barrel 28, further travel of the drive bar 26 in the distal direction is prevented by the inner barrel 28. At this point, the drive spring 38 functions to hold the drive bar 26 against the inner barrel 28 until a subsequent injection is initiated by the user.

Referring now with cross reference to FIGS. 2 and 3, the injector 10 includes a vacuum control system having a vacuum pump 42 for creating suction in a suction compartment 44 that surrounds the injector tip 34. Signals from the vacuum control system can be sent to a computer processor (not shown) for use in monitoring compliance to a therapeutic regimen. As shown, a battery 46 is provided to power the vacuum pump 42. Also shown, a first switch 48 that is user operable is included to control the vacuum pump 42. A printed circuit board 50 is provided containing a portion of an electrical circuit (shown in FIG. 5) that connects the battery 46 and vacuum pump 42 to the first switch 48. For the present invention, the electrical circuit includes an electrical connection to the drive bar 26 and an electrical connection to the inner barrel 28. Specifically, the negative terminal of the battery 46 is electrically connected to the proximal tube 24, which in turn, via drive spring 38, is in electrical contact with the drive bar 26. Thus the drive bar 26 is in electrical contact with the negative terminal of the battery 46 at all times. Further, as shown, wire 51 is provided to maintain an electrical connection between the inner barrel 28 and the electrical circuit on the printed circuit board 50. Importantly for the present invention, both the drive bar 26 and inner barrel 28 are constructed of electrically conductive materials. Preferably, the distal tube 22 is made of a non-conductive material such as plastic to insulate the inner barrel 28 from the proximal tube 24 when the drive bar 26 is not in contact with the inner barrel 28. With this cooperation of structure, the vacuum pump 42 can be activated and deactivated in a predetermined manner in response to the controlled movement of the first switch 48 and contact between the drive bar 26 and inner barrel 28 (referred herein as the second switch 52).

Figure 5:
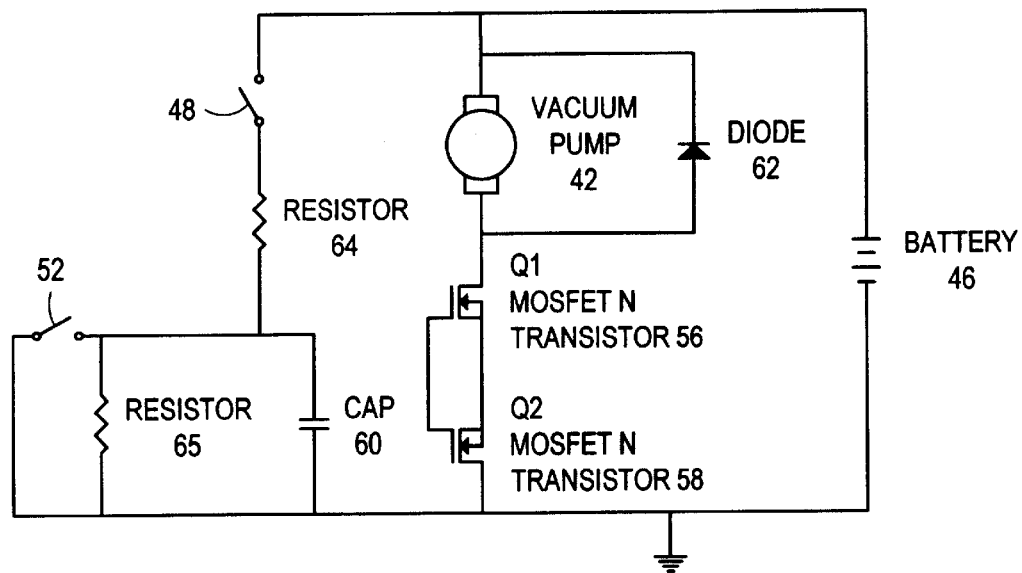
FIG. 5 is a schematic diagram of an electrical circuit for controlling a vacuum motor in accordance with the present invention.

A suitable electrical circuit for controlling the vacuum system in accordance with the present invention is shown schematically in FIG. 5. As shown, the circuit includes the first switch 48 and the second switch 52 described above. By cross referencing FIGS. 2–5, it can be seen that the first switch 48 is user operable and is moveable between an ON position wherein current flows through the first switch 48 (i.e. the first switch 48 is closed) and an OFF position. A return spring 54 is provided to bias the first switch 48 in the OFF position. In this embodiment, the return spring 54 also functions as one of the contacts for the first switch 48. The other contact of the first switch 48 is mounted on the printed circuit board 50. The second switch 52 is established by the contact of the inner barrel 28 with the drive bar 26. When the inner barrel 28 contacts the drive bar 26, the second switch 52 is in the ON position and current flows through the second switch 52 (i.e. the second switch 52 is closed). Conversely, when the inner barrel 28 is separated from the drive bar 26, the second switch 52 is in the OFF position and no current flows through the second switch 52 (i.e. the second switch 52 is closed).

Referring now to FIG. 5, it is to be appreciated that the electrical circuit is configured to pass current from the battery 46 to the vacuum pump 42 when the first switch 48 is in its ON position and the second switch 52 is in its OFF position. Further, the electrical circuit is configured to prevent current from passing through the vacuum pump 42 when the first switch 48 is in its ON position and the second switch 52 is in its ON position. Additionally, the electrical circuit is configured to prevent current from passing through the vacuum pump 42 whenever the first switch 48 is in its OFF position.

To function in the manner described above, the electrical circuit includes a pair of MOSFET n type transistors 56, 58. Preferably, the transistors 56, 58 are both ultra low threshold (0.9 V) so that current can be passed to the vacuum pump 42 even when the battery 46 has emptied to below 2.0 V. Those skilled in the art will appreciate that only one MOSFET transistor 56, 58 is required to control the vacuum pump 42. The second MOSFET transistor 56, 58 is added to prevent damage to the first MOSFET transistor 56, 58 from excessive heat if the battery 46 is installed backwards.

A capacitor 60 is provided to hold the voltage at the gates of the transistors 56, 58 steady to ensure steady power to the vacuum pump 42. Diode 62 is provided to protect the transistors 56, 58 by shunting any negative kick generated by the effect of the inductance of the DC motor windings in the vacuum pump 42 in response to rapidly changing current. A large resistor 64 is provided to limit power loss when the first switch 48 and second switch 52 are both closed. Resistor 65 is provided in parallel to switch 52 and capacitor 60. Resistor 65 biases the gate of the transistors 56, 58 such that they are non-conducting (vacuum pump 42 is off) when the first switch 48 is open. When the first switch 48 and second switch 52 are open, the gate is pulled low to ground through the resistor 65. The value of the resistor 65 is chosen such that with the selected value for resistor 64 and when the injector 10 is cocked and the safety is pressed (switch 52 open and switch 48 closed), the voltage at the gates of transistors 56, 58 is as close to the voltage of the battery 46 as possible. An optional circuit can be used with the present invention to drive an LED when the vacuum pump 42 is running. The LED can be used by the operator to indicate when an injection is complete.

Figure 6:
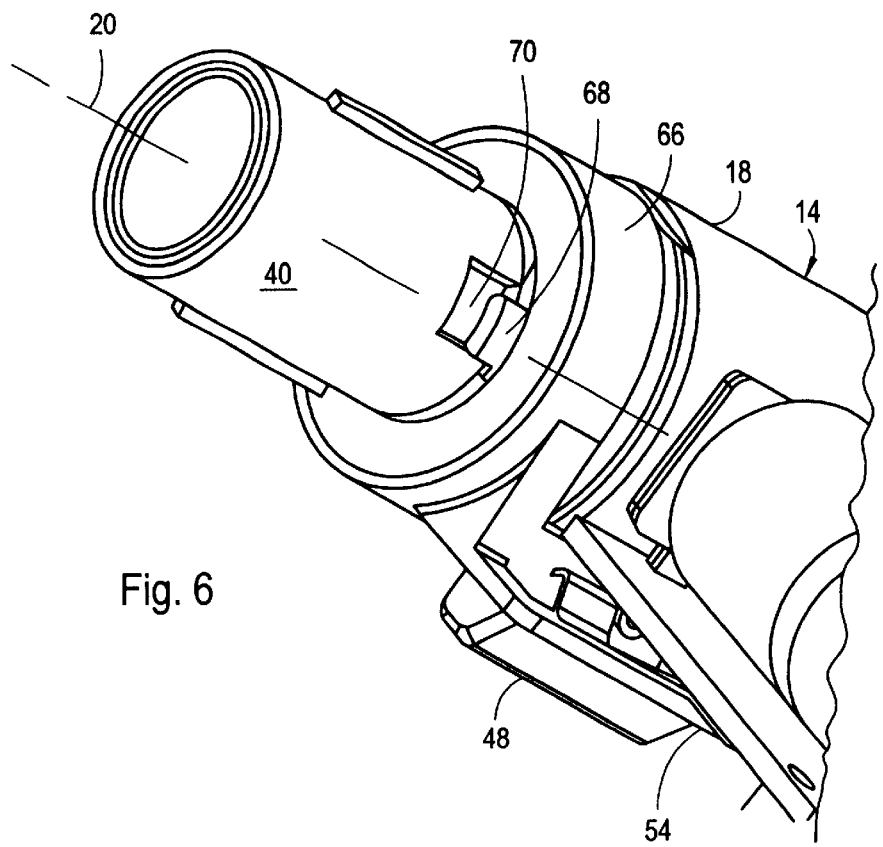
FIG. 6 is an enlarged, perspective view of the proximal portion of the device of the present invention showing an embodiment of the safety interlock feature of the present invention.

Referring now to FIG. 6, it can be seen that user operable first switch 48 also functions as a safety release button for the firing cap 40. As shown, an interlock ring 66 is mounted on the proximal end 18 of the housing 14 for rotation about the longitudinal axis 20 of the housing 14. As such, the interlock ring 66 is interposed between the proximal end 18 of the housing 14 and the firing cap 40. As further shown, the interlock ring 66 is attached to the first switch 48 for rotation about the longitudinal axis 20 of the housing 14 in response to movements of the first switch 48. A tab 68 projects proximally from the interlock ring 66 for engagement with a slot 70 formed in the firing cap 40. When the first switch 48 is depressed (i.e. moved to its ON position), the interlock ring 66 is rotated to align the tab 68 of the interlock ring 66 with the slot 70 of the firing cap 40. With the tab 68 and slot 70 aligned, the firing cap 40 is armed (i.e. capable of being depressed to initiate an injection). The return spring 54, which biases the first switch 48 in the OFF position, also biases the interlock ring 66 into a position where the tab 68 and slot 70 are misaligned to thereby disarm and lock the firing cap 40 whenever the first switch 48 is not depressed by the user.

Figure 7:
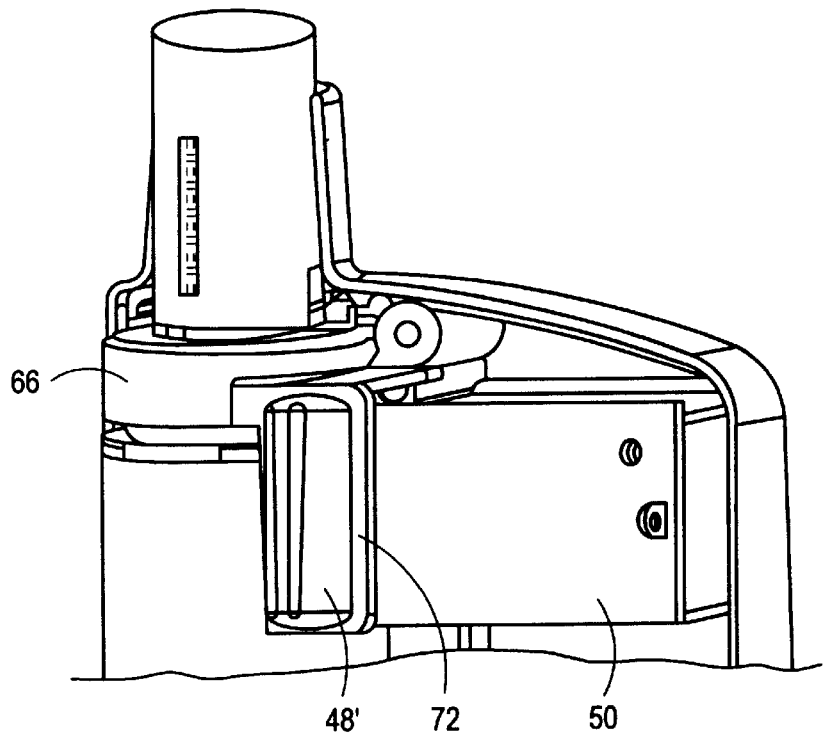
FIG. 7 is an enlarged, perspective view of the proximal portion of a device in accordance with the present invention showing an alternate embodiment having a miniature detector switch and a compression return spring.
Figure 8:
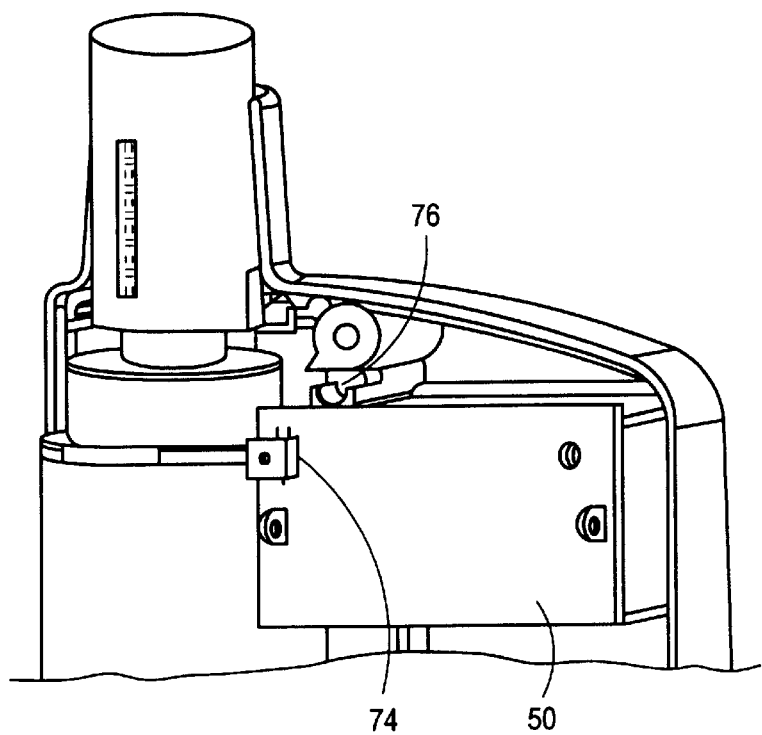
FIG. 8 is an enlarged, perspective view of the proximal portion of the device shown in FIG. 7 with portions removed for clarity.

Referring now to FIGS. 7 and 8, an alternative embodiment for the first switch (designated first switch 48') is shown. In this embodiment, the first switch 48' includes a lever 72 that is attached to the interlock ring 66 and a miniature detector switch 74 that is mounted on the printed circuit board 50. It is to be appreciated that depressing the lever 72 results in both the rotation of the interlock ring 66 to disarm the firing cap 40 and the closing of the miniature detector switch 74 (allowing current to flow through the miniature detector switch 74). A housing 76 is provided for containing a compression spring (not shown) to bias the lever 72 away from the miniature detector switch 74. Thus, the first switch 48' shown in FIGS. 7 and 8 functions in essentially the same manner as the first switch 48 shown in FIG. 2.

In addition to the embodiments described above for first switch 48 and 48', it is to be appreciated by those skilled in the art that other types of switches that are capable of both closing an electrical circuit and moving an interlock ring 66 can be used in the present invention. For example, an electrical switch (such as a simple membrane dome switch, not shown) could be used to close the electrical circuit and initiate a vacuum actuator (not shown) to rotate the interlock ring 66. A parallel switch activated by the movement of the interlock ring 66 can be provided to maintain the vacuum pump 42 until the drive bar 26 contacts the inner barrel 28.

To perform an injection, as best understood with cross reference to FIGS. 3, 4 and 6, the injector 10 generally begins in the uncocked configuration, with the drive bar 26 in contact with the inner barrel 28 (uncocked configuration shown in FIG. 4). In the uncocked configuration, both the first switch 48 and the second switch 52 are in the ON position, and consequently, the vacuum pump 42 is inactive. Upon cocking the injector 10, the bearings 39 engage and hold the drive bar 26 near the proximal end 18 of housing 14 (cocked configuration shown in FIG. 3). Thus, in the cocked configuration, the drive bar 26 is separated from the inner barrel 28 and accordingly, the second switch 52 is in the OFF position. Further, during cocking, the drive bar 26 moves the firing cap 40 until the firing cap 40 is positioned proximally to the interlock ring 66. As such, the return spring 54 causes both the first switch 48 to move into the OFF position and the interlock ring 66 to move to a position where the tab 68 of the interlock ring 66 and the slot 70 of the firing cap 40 are misaligned. Thus, when the injector 10 is in the cocked configuration, the vacuum pump 42 is inactive (because both the first switch 48 and the second switch 52 are OFF) and the firing cap 40 is disarmed and locked.

Once the injector 10 is in the cocked configuration, the user can position the injector tip 34 to a preselected area of skin and depress and hold the user operable first switch 48. Upon depressing the first switch 48, the vacuum pump 42 will be activated (first switch 48 ON, second switch 52 OFF) to provide suction in the suction compartment 44. Further, as indicated above, the firing cap 40 will be armed. At this point, release of the first switch 48 by the user will deactivate the vacuum pump 42, allowing the user to reposition the injector tip 34. Specifically, upon release of the first switch 48, the return spring 54 will cause both the first switch 48 to return to the OFF position and the interlock ring 66 to return to a position where the firing cap 40 will be disarmed and cocked.

While the first switch 48 is depressed and held by the user, the vacuum pump 42 remains activated and the firing cap 40 remains armed. Thus, by holding the first switch 48 ON and depressing the firing cap 40, the user can inject the medicament. Upon depressing the firing cap 40, the bearings 39 holding the drive bar 26 are disengaged and the drive bar 26 is released. Further, depressing the firing cap 40 causes the tab 68 of the interlock ring 66 to extend into the slot 70 in the firing cap 40. Importantly, this prevents the interlock ring 66 from rotating. As such, after the firing cap 40 is depressed, the first switch 48 is held in the ON position due to the inability of the interlock ring 66 to rotate. Consequently, once the user depresses the firing cap 40, the vacuum pump 42 remains activated for the entire duration of the injection, irregardless of the whether the user releases the first switch 48.

As indicated above, depressing the firing cap 40 releases the drive bar 26 for translation along the housing 14. Specifically, the drive bar 26 travels until it contacts the inner barrel 28, terminating the injection. This contact with the inner barrel 28 closes the second switch 52, automatically deactivating the vacuum pump 42 (both first switch 48 and second switch 52 ON). At this point, the injector 10 is in the uncocked configuration, and after replacing the injected medicament, the above described operation steps can be repeated to perform another injection.

While the particular device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A vacuum control system for a jet injector which comprises:
    a power source;
    a vacuum pump;
    a first switch moveable between an ON position and an OFF position;
    a second switch moveable between an ON position and an OFF position;
    an electrical means for passing a current from said power source to said vacuum pump to operate said vacuum pump, said electrical means having a first configuration for passing current therethrough when said first switch is in its ON position and said second switch is in its OFF position, and said electrical means having a second configuration for preventing current from passing therethrough when said first switch is in its ON position and said second switch is in its ON position; and
    a mechanical means for sequentially turning said first switch from its OFF position to its ON position and subsequently turning said second switch from its OFF position to its ON position.

2. A system as recited in claim 1 wherein said mechanical means is said jet injector.

3. A system as recited in claim 1 wherein said mechanical means comprises:
    a substantially hollow tube;
    a drive bar mounted inside said tube for movement between a first position and a second position;
    a drive mechanism mounted inside said tube for urging said drive bar toward said second position;
    a mechanism for holding said drive bar in said first position;
    a firing cap mounted on said tube; and
    a safety release button mounted on said tube for arming said firing cap to selectively disengage said holding mechanism and release said drive bar for movement from said first position to said second position.

4. A system as recited in claim 3 wherein said first switch is said safety release button.

5. A system as recited in claim 3 wherein said drive bar moves said second switch into its ON position when said drive bar is in its second position.

6. A device for injecting a medicament into a patient, said device comprising:
    a substantially hollow tube having a distal end and a proximal end;
    a drive bar mounted inside said tube for movement from a first position near said proximal end of said tube to a second position near said distal end of said tube, said movement for expelling medicament from said tube;
    a vacuum pump;
    a user operable switch moveable between an ON configuration and an OFF configuration; and
    an electrical means for activating said vacuum pump when said drive bar is at said first position and said user operable switch is in said ON configuration, and deactivating said vacuum pump when said drive bar is at said second position and said user operable switch is in said ON configuration.

7. A device as recited in claim 6 further comprising a means for biasing said user operable switch in said OFF configuration.

8. A device as recited in claim 7 wherein said means for biasing said user operable switch in said OFF configuration is a return spring.

9. A device as recited in claim 6 wherein said electrical means comprises a conductive element positioned inside said tube for contact with said drive bar when said drive bar is at said second position.

10. A device as recited in claim 9 wherein said conductive element is an inner barrel.

11. A device as recited in claim 6 wherein said electrical means is configured to deactivate said vacuum pump when said drive bar is at said first position and said user operable switch is in said OFF configuration.

12. A device as recited in claim 6 wherein said electrical means comprises an electrical circuit including two MOS-FET n transistors.

13. A device as recited in claim 6 further comprising;
    a drive mechanism mounted inside said tube for urging said drive bar toward said second position;
    a cocking mechanism for holding said drive bar in said first position;
    a firing cap mounted on said tube, said firing cap moveable between a first configuration wherein said drive bar is held in said first position and a second configuration wherein said drive bar is released from said first position; and
    a means for releasably locking said firing cap in said first configuration.

14. A device as recited in claim 13 wherein said tube defines a longitudinal axis, said firing cap is formed with a slot, and said means for releasably locking said firing cap comprises:
    a locking ring rotatably mounted on said proximal end of said tube, said locking ring formed with a tab, and said locking ring attached to said user operable switch to rotate about said longitudinal axis in response to movements of said user operable switch, with said tab and said slot being aligned to arm said firing cap when said user operable switch is in the ON position, and said tab and said slot being misaligned to lock said firing cap when said user operable switch is in the OFF position.

15. A vacuum control and safety interlock system which comprises a medicament injector having a vacuum pump and a firing cap mounted thereon, said firing cap moveable from an initial position to a depressed position to cause said injector to inject a medicament, said system comprising:
    a user operable switch moveable between an ON configuration and an OFF configuration;
    an electrical means for activating said vacuum pump after said user operable switch has been moved to said ON configuration; and
    a means for locking said firing cap in said initial position when said user operable switch is in said OFF configuration and unlocking said firing cap when said user operable switch is in said ON configuration.

16. A system as recited in claim 15 wherein said firing cap is formed with a slot and said locking means comprises:

a locking ring having a tab extending therefrom, said locking ring mounted on said injector for relative movement thereto, said locking ring attached to said user operable switch to move therewith and cause said tab and said slot to align and unlock said firing cap when said user operable switch is in said ON configuration, said locking ring attached to said user operable switch to cause said tab and said slot to misalign and lock said firing cap when said user operable switch is in said OFF configuration.

17. A system as recited in claim 15 wherein the injector has an internal switch and a mechanical means for turning the internal switch from an OFF configuration to an ON configuration upon completion of an injection of medicament, and wherein said system further comprises:

an electrical means for activating said vacuum pump when said user operable switch is in its ON configuration and said internal switch is in its OFF configuration and deactivating said vacuum pump when said user operable switch is in its ON configuration and said internal switch is in its ON configuration.

18. A system as recited in claim 17 wherein said electrical means comprises an electrical circuit including two MOSFET n transistors.

19. A system as recited in claim 17 wherein said electrical means is configured to deactivate said vacuum pump when said internal switch is in said OFF configuration and said user operable switch is in said OFF configuration.

20. A system as recited in claim 15 further comprising a return spring to bias said user operable switch to said OFF configuration.

21. A system as recited in claim 15 further comprising a means for driving an LED when said vacuum pump is activated.

* * * * *